United States Patent [19]

Catapano

[11] Patent Number: 5,116,814
[45] Date of Patent: * May 26, 1992

[54] PROCESS FOR THE REMISSION OF SYMPTOMS ASSOCIATED WITH AIDS

[76] Inventor: Salvatore J. Catapano, 66 S. Brush Dr., Valley Stream, N.Y. 11581

[*] Notice: The portion of the term of this patent subsequent to Dec. 8, 2004 has been disclaimed.

[21] Appl. No.: 698,196

[22] Filed: May 6, 1991

Related U.S. Application Data

[60] Continuation of Ser. No. 382,673, Jun. 28, 1989, abandoned, which is a continuation-in-part of Ser. No. 804,858, Dec. 5, 1985, Pat. No. 4,711,876, and a continuation-in-part of Ser. No. 562,458, Aug. 1, 1990, abandoned, which is a continuation of Ser. No. 453,104, Dec. 20, 1989, abandoned, which is a continuation of Ser. No. 344,508, Apr. 20, 1989, abandoned, which is a continuation of Ser. No. 214,835, Jul. 1, 1988, abandoned, which is a continuation of Ser. No. 133,176, Dec. 11, 1987, abandoned, which is a continuation of Ser. No. 17,586, Feb. 24, 1987, abandoned, which is a division of Ser. No. 410,593, Aug. 23, 1982, abandoned, which is a continuation-in-part of Ser. No. 925,536, Jul. 17, 1978, abandoned, which is a continuation-in-part of Ser. No. 855,191, Nov. 28, 1977, abandoned.

[51] Int. Cl.$^5$ .................. A61K 39/00; A61K 39/02
[52] U.S. Cl. .................. 514/2; 514/885; 424/92
[58] Field of Search .......... 424/88, 92; 514/2, 21, 514/885; 128/154; 530/820, 825

[56] References Cited

U.S. PATENT DOCUMENTS 4,711,876 12/1987 Catapano .................. 514/2

Primary Examiner—Nathan M. Nutter
Attorney, Agent, or Firm—Foley & Lardner

[57] ABSTRACT

A method of treating a human patient to effect the remission of AIDS, which comprises parenterally administering to the AIDS patient typhoid vaccine in a therapeutically effective amount which is sufficient to provide immunostimulating activity.

13 Claims, No Drawings

5,116,814

PROCESS FOR THE REMISSION OF SYMPTOMS ASSOCIATED WITH AIDS

RELATED U.S. APPLICATION DATES

This application is a continuation of application Ser. No. 382,673, filed June 28, 1989 and now abandoned which application is a continuation-in-part of U.S. application Ser. No. 804,858, filed Dec. 5 1985 and now U.S. Pat. No. 4,711,876.

This application is also a continuation-in-part application of Ser. No. 07/562,458, filed Aug. 1, 1990 and now abandoned; which is a continuation application of Ser. No. 07/453,104, filed Dec. 20, 1989, now abandoned; which is a continuation application of Ser. No. 07/344,508, filed Apr. 20, 1989, now abandoned; which is a continuation application of Ser. No. 07/214,835, filed July 1, 1988, now abandoned; which is a continuation application of Ser. No. 07/133,176, filed Dec. 11, 1987, now abandoned; which is a continuation application of Ser. No. 07/017,586, filed Feb. 24, 1987, now abandoned; which is a divisional application of Ser. No. 06/410,593, filed Aug. 23, 1982, now abandoned; which is a continuation-in-part application of Ser. No. 05/925,536, filed July 17, 1978, now abandoned; which is a continuation-in-part application of Ser. No. 05/855,191, filed Nov. 28, 1977, now abandoned.

BACKGROUND OF THE INVENTION

This invention relates to a process with an FDA approved adjuvant which is non-toxic to bring about the stimulation of leukocytes which inactivate the AIDS condition. Currently, there are no drugs available anywhere that have been shown to bring about the remission of AIDS, although the search for such drugs is being pursued vigorously. Some drugs have been found that inhibit the action of HTLV-III, but these do not lead to clinical improvement. A test performed by the Public Health Service, National Institutes of Health, National Cancer Institute, Bethesda, Md. on typhoid vaccine is reported in a May 12, 1976 letter from Dr. Michael A. Chirigos to Dr. John Douros as follows:

"We have completed our initial experimental testing of typhoid vaccine for immunostimulating activity. The test system we used was a homograft tumor response. This is similar to a skin graft where if the skin graft is not compatible to the host, the host will reject it by an immunological response.

The immune cells involved in the immunological response are T-Lymphocyte macrophages or B-Lymphocytes. Our results show that typhoid vaccine stimulates macrophages. The stimulation evoked by typhoid vaccine was as good or better than the immune-stimulator we use for control.

The results . . .[indicate] that is has the capacity to stimulate macrophage cell activity."

"T" Lymphocytes are responsible for cellular immunity. "B" Lymphocytes are responsible for humoral immunity. Two basic, but closely allied, types of immunity occur in the body. In one of these, the body develops circulating antibodies, which are globulin molecules that are capable of attacking the invading agent. This type of immunity is called "Humoral Immunity". The second type of immunity is achieved through the formation of large numbers of highly specialized lymphocytes that are specifically sensitized against the foreign agent. These sensitized lymphocytes have the special capability to attach to the foreign agent and to destroy it. This type of immunity is called cellular immunity or, sometimes, lymphocytic immunity.

Typhoid vaccine is antigenic. Furthermore, the process of antigenicity probably depends upon regularly recurring prosthetic radicals on the surface of the large molecule, which perhaps explains why proteins and many polysaccharides are antigenic, for they both have this characteristic.

Though most of the lymphocytes in the normal lymphoid tissue look alike when studied under the microscope, these cells are distinctly divided into two separate populations. One of the populations is responsible for forming the sensitized lymphocytes that provide cellular immunity and the other for forming the antibodies that provide humoral immunity. Both of these types of lymphocytes are derived originally in the embryo from lymphocytic stem cells in the bone marrow. The descendants of the stem cells eventually migrate to the lymphoid tissue. Before doing so, however, those lymphocytes that are eventually destined to form sensitized lymphocytes first migrate to and are preprocessed in the thymus gland, for which reason they are called "T" lymphocytes. These are responsible for cellular immunity. The other population of lymphocytes, those that are destined to form antibodies, is processed in some unknown area of the body, possibly the liver and spleen. For this reason, this population of lymphocytes is called the "B" lymphocytes, and they are responsible for humoral immunity.

SUMMARY OF THE INVENTION

In accordance with this invention, there is provided a process in which typhoid vaccine is used by itself and not in conjunction with any other treatment, including radiation therapy or chemotherapy, for the remission of symptoms associated with AIDS. The typhoid vaccine is administered parenterally in an amount of from about 0.02 to about 2.5 c.c.

Typhoid vaccine is marketed by Wyeth Laboratories. Each c.c. contains not more than 1,000 million Salmonella Typhosa (Ty-2 strain) organisms, killed and suspended in buffered sodium chloride injection. The preservative is 0.5% phenol. It is described beginning at page 2209, Physicians' Desk Reference, Medical Economics Company (1987).

DETAILED DESCRIPTION OF THE INVENTION

It has been found that a remission of the symptoms of a person afflicted with AIDS, may be achieved by the parenteral administration, in multiple injections, of typhoid vaccine in a amount of from about 0.02 to about 2.5 c.c. with no observed toxicity. This procedure stimulates not only humoral immune response but also the reticuloendothelial system body defense mechanisms within the host so that it is capable of combatting AIDS within its body.

Since one object of this invention is to enhance the immune response of the body to combat AIDS, any other treatment, such as chemotherapy and radiation therapy which would reduce the immune response of the body, should be discontinued. It is believed that a chemotherapeutic agent may be helpful after the AIDS symptoms are in remission and the body's immune system is sufficiently strong.

In treating for the remission of symptoms associated with AIDS, a thorough medical history of the patient should be obtained and the patient should be given a complete physical examination. If there is evidence of the existence of pneumocystis carinii pneumonia (PCP), an infection of the lungs which has symptoms similar to other forms of pneumonia; and/or a rare type of cancer known as Kaposi's sarcoma (KS) which usually occurs anywhere on the surface of the skin or in the mouth, these should be noted. In early stages, KS may look like a bruise or blue-violet or brownish spot. The spot or spots persist, and may grow larger. KS may spread to or appear in other organs of the body. X-rays of the affected areas should be taken. The patient's temperature should be taken just prior to the administration of the typhoid vaccine. A chest X-ray and a broad spectrum blood test should also be obtained.

Initially, an injection of about 0.2 c.c. subcutaneously should be given to test for idiosyncrasy or existing allergy to the typhoid vaccine preparation. An allergy to the typhoid vaccine may appear as a large red spot at the area of injection. The patient should be observed for at least about 3-4 hours to determine whether there is an adverse reaction to the injection.

If there is no adverse reaction to the test injection, the patient should be started on the treatment generally following the protocol shown in Table I.

TABLE I

Protocol for the treatment of the acquired immunedefficiency syndrome with typhoid vaccine.

Day 1 Injection of 0.2 cc subcutaneously to test for idiosincrasy or existing allergy to the typhoid vaccine preparation.
Day 4 Injection of 0.3 cc subcutaneously.
Day 8 Injection of 0.4 cc subcutaneously.
Day 12 Injection of 0.5 cc subcutaneously.
Day 16 Injection of 0.6 cc subcutaneously.
Day 20 Injection of 0.75 cc subcutaneously.
Day 24 Injection of 0.75 cc subcutaneously.
Day 32 Injection of 0.75 cc subcutaneously and 0.25 cc also subcutaneously 1 hour later.
Day 40 Injection of 0.5 cc subcutaneously, 0.5 cc 1 hour later subcutaneously and 0.25 ½ hour later subcutaneously.
Day 48 Injection of 0.6 cc subcutaneously, 0.4 cc 1 hour later and 0.5 cc 1 hour later also subcutaneously.
Day 54 Injection of 0.5 cc subcutaneously, 0.4 cc 1 hour later and 0.6 cc 1 hour later.
Day 60 Injection of 0.4 cc subcutaneously, 0.6 cc subcutaneously 1 hour later and 0.4 cc 1 hour later subcutaneously.
Day 68 Injection of 0.75 cc subcutaneously, 0.5 cc 1 hour later and 0.25 cc 1 hour later subcutaneously.
Day 76 and every week thereafter for four weeks: 0.5 cc subcutaneously, 0.5 cc 1 hour later and then 0.25 cc subcutaneously.

It must be emphasized that the protocol listed in Table I is only a general outline of treatment in accordance with this invention. Depending on the response and clinical picture, a patient may be switched from weekly to bi-weekly injections and from single to multiple or from multiple to single injections on the day of treatment.

The patient should be continually monitored to determine whether he or she has contracted any opportunistic infections such as PCP or thrush. If a patient contracts PCP or thrush, he or she can be treated with an appropriate antibiotic using known procedures. The patient should also be checked for the presence of anemia which can also be treated using known procedures.

A periodic (2-3 weeks) blood test should be taken and that information, together with the clinical evaluation of the patient's symptoms, should be used to determine the course of treatment. Particular attention should be given to the patient's white blood count and, more importantly, to the patient's differential blood count. If the white blood count and the differential blood count show improvement, the treatment should be continued substantially as shown in Table I. If the blood counts do not show improvement, or show a decline, the patient should be more closely monitored to determine whether there are other problems present in addition to the AIDS infection.

If the patient has undergone chemotherapy (e.g. AZT) or radiation therapy, he or she must usually be monitored more closely. Initially the patient should receive a detailed chest X-ray and should be checked for anemia. Treatment should then begin as previously described. The patient must be monitored closely for signs of infection and the blood must also be closely monitored for any signs of abnormality.

Blood transfusions are often required after chemotherapy such as AZT. Washed, packed cells are advantageously employed in the transfusion. The need for a transfusion is indicated by a low red blood count, low hemaglobin count and/or low hematocrit count. The frequency of the transfusion will be dictated by the above blood counts.

The patient should also be watched closely with particular attention being given to body temperature and blood pressure. An indication that the vaccine is taking effect is an elevation of body temperature within the range of about 99.6°-103° F. The immune response of the patient can be monitored using a periodic quantitative agglutination titer, e.g. a widal test should be made.

Advantageously the protocol shown in Table I is followed. Generally the protocol requires injections spaced about four (4) days apart for the first twenty four (24) days. During the first twenty four (24) days the quantity of typhoid vaccine administered is increased from about 0.3 to about 0.75 c.c. per administration. Beginning at about day thirty two (32), the patient is given a series of multiple injections, each series occurring approximately eight (8) days apart. For example, on day thirty two (32), the patient is first injected with 0.75 c.c. subcutaneously, and then one (1) hour later, is injected with 0.25 c.c. subcutaneously. Beginning at about day forty (40), a series of three (3) injections is given approximately every eight (8) days until about day seventy six (76). At day seventy six (76,) and every week thereafter for four (4) weeks, the patient receives multiple injections substantially as shown in Table I.

Once the patient is felt to have reached a stable state, a maintenance schedule can be instituted. The maintenance schedule comprises a series of multiple injections; 0.4 c.c. subcutaneously, 0.4 c.c. one (1) hour later, and 0.5 c.c. one (1) hour later, once a week until about the sixth (6) month of treatment. At that point, maintenance continues with the same series of three (3) multiple injections every other week for approximately two (2) months. By about the eighth (8) month of treatment, maintenance continues with administration every three (3) weeks, and by about the eleventh (11) month of treatment the protocol is given once (1) a month. After about fifteen months it is believed that maintenance injections can be given every three months for an indefinite period. The exact length of treatment is still undefined but after the individual becomes asymptomatic, the maintenance dose is gradually tapered and eventually discontinued. If a relapse should occur, the protocol is restarted.

It must be understood that the above-described protocol is only a general guideline and that modifications may take place at the treating physician's discretion. However, such discretion is well within the ordinary ability of a treating physician.

Again, it must be emphasized that if the patient has been previously treated with chemotherapeutic or radiation therapy, especially therapy that suppresses the immune system, that patient usually must be watched more closely than a patient who has not undergone such treatment.

While the permanent eradication of AIDS may be impossible, by a systematic course of injection of typhoid vaccine in accordance with the practice of this invention, the remission of the symptoms associated with AIDS will continue indefinitely or the AIDS will reach such a low level that subsequent antibiotic or chemotherapy treatments may result in 100% kill. Subsequent treatment by this process will be dependent in part on the observed response of the patient to the original protocol.

To treat a patient for immunization against AIDS, the patient should be examined as previously described. If the patient is in generally good health, typhoid vaccine in an amount of from about 0.2 to about 2.5 c.c. is administered. After three to four weeks, an agglutination or other seriological test should be performed in order to ascertain whether the patient shows a positive reaction to the vaccine. Not more than three months after injection of the vaccine, or sooner depending on the general health of the patient, an additional injection of the typhoid vaccine should be administered. This injection should be of a lesser dosage than the initial injection. Within nine months from the initial injection of the typhoid vaccine, another agglutination or seriological test should be performed to ascertain if immunization is present.

Clumping should be shown undiluted and at least 12 dilutions—from 1:2 through 1:12. Should there be an absence of immunization, the patient is again given an injection of typhoid vaccine, the amount to be determined by reference to the reaction of the patient to the prior injections. In addition to treating AIDS, the above protocol can be used to treat other immunosuppressive diseases such as arthritis, multiple sclerosis, cystic fibrosis, alzheimer's disease, etc.

The following examples illustrate the immunostimulating activity achieved by the practice of this invention.

EXAMPLE 1

Twelve AIDS patients were treated following substantially the above-described protocol. Their length of treatment ranged from about five (5) weeks to about nine (9) months. Their results are shown in Table II below.

From Table II it is clearly seen that treatment of AIDS patients using this invention effects the remission of symptoms associated with AIDS.

EXAMPLE 2

The white blood count and differential blood count for fifteen (15) AIDS patients were monitored over a period of from about four (4) weeks to about seven (7) or eight (8) months. The "before" and "after" results are shown in Table III below. Those results clearly indicate that treatment of AIDS patients in accordance with this invention results in an increased white blood count and importantly, improved differential blood counts indicating a strengthened immune system.

While various advantageous embodiments and examples have been chosen to illustrate the invention, it will be understood by those skilled in the art that various modifications can be made therein without departing from the scope of the invention as defined in the appended claims.

TABLE II

| Patient | K.S. | Night Sweats/ Fever | Constant Sore Throat | Weight Loss/Gain | Thrush |
|---|---|---|---|---|---|
| (1) | Initially had lesions in both feet and toes. At 9 months, only the two big toes remain affected. | | Disappeared after about 4 weeks | Gained 9 pounds at 6 months. Does not want to gain any more weight | Gone at 6 weeks |
| (2) | Present in the beginning in small patches in arms and trunk. Patches are getting lighter in color and flatter in thickness at 8 weeks | | | | |
| (3) | | | | | Mild thrush disappeared in 5 weeks |
| (4) | | | | | |
| (5) | | | | | |
| (6) | Lentil-shaped lesions in both legs are slowly receding at 3 months | | Persistent sore throat gone at 5 weeks | | |
| (7) | | | Low grade fever gone after several weeks | | |
| (8) | Had painful and itchy lesions in glans and perianal area with oozing material in both | Recurring fever gone after several weeks. | | No change but patient exercises actively | |

TABLE II-continued

|     | | | | | |
| --- | --- | --- | --- | --- | --- |
|     | areas. At 3 months, lesions are dry, non-painful and non-itching Large spots on the legs are showing streaks of normal looking skin and thus appear fragmented. | | | | |
| (9) | Initially had nodular lesions, one of them ulcerated on left foot, which oozes. Flat lesions on trunk and arms. At two months, lesions have stopped draining, are shrinking and drying Surgically removed lesion shows no sign or recurence 2 weeks later | | | | |
| (10) | | Night sweats gone at 6 weeks | | | |
| (11) | | Night sweats gone at 5 weeks | | Gained 4 lbs in 2 months | |
| (12) | | | Persistent sore throat gone at 6 weeks | Gained 3 lbs at 6 weeks | Mild thrush gone at 6 weeks |

| Patient | Swollen Glands | Persistent Cough | Fatigability | Miscellaneous |
| --- | --- | --- | --- | --- |
| (1) | Bilateral inquinal adenc-pathy began to disappear at 8 weeks. Gone at 9 months | | Unable to work for more than 2 hours at start of treatment. At 6 weeks, was able to work full time and even overtime. Has returned to weightlifting | |
| (2) | | | Feeling more energetic at 8 weeks | |
| (3) | | | Easy fatigability gone at 3 weeks | Depression gone at 5 weeks |
| (4) | Swelling in bilateral inquinal nodes gone at 3 months. Lert auxiliary node has shrunk about 50% at 3 months | | Mild fatigue gone at 6 weeks | Appetite is significantly better |
| (5) | | | More energetic at 3 months; performing better at work and expanding business | |
| (6) | | | | |
| (7) | Bilateral posterior nodes shrank about 50% at 8 weeks. Swelling gone at 14 weeks | | At beginning, very exhausted at all times and barely able to carry on job. Fatigue 90% gone at 6 weeks and able to perform work. Reports "excellent condition" | |
| (8) | Bilateral posterior cervical nodes have shrunk more than 75% at 3 months | | Fatigue prominent at the beginning is slowly diminishing at 3 months | |
| (9) | | | Moderate fatigue gone at 2 months. Feels stronger and healthier | Appetite returned at 2 months |
| (10) | Swollen left inquinal nodes unchanged at 6 weeks | | Moderate to severe fatigability and onset. About to lose his job. Feels much better at 6 weeks and is catching up with work. | |
| (11) | Big node on left side of neck still present at 2 months but softer in consistency | | Fatigue present at beginning is much improved at 2 months | Headaches gone at 6 weeks Appetite increased significantly at 5 weeks |
| (12) | | Persistent cough gone at 6 weeks | Marked fatigue gone at 6 weeks | Appetite much improved at 6 weeks |

TABLE III

| Patient | WHITE BLOOD COUNT (× 1000) | DIFFERENTIAL BLOOD COUNT | | | | | |
|---|---|---|---|---|---|---|---|
| | | Segmented (neutrophils) | Lymphocytes | Monocytes | Eosinophils | Basophils | Bands |
| Harold | | | | | | | |
| Before | 2.9 | 72 | 22 | 5 | 1 | 0 | 0 |
| After | 3.7 | 54 | 44 | 1 | 1 | 0 | 0 |
| Giacomo | | | | | | | |
| Before | 3.1 | 78 | 21 | 1 | 0 | 0 | 0 |
| After | 4.9 | 51 | 47 | 2 | 0 | 0 | 0 |
| Larry | | | | | | | |
| Before | 2.6 | 71 | 17 | 5 | 5 | 2 | 0 |
| After | 6.2 | 70 | 27 | 1 | 2 | 0 | 0 |
| Kevin | | | | | | | |
| Before | 1.3 | 60 | 30 | 1 | 0 | 2 | 7 |
| After | 6.2 | 55 | 41 | 1 | 3 | 0 | 0 |
| Ted | | | | | | | |
| Before | 3.23 | 63 | 33 | 0 | 2 | 0 | 2 |
| After | 5.1 | 53 | 43 | 2 | 1 | 0 | 1 |
| Andy | | | | | | | |
| Before | 1.7 | 78 | 14 | 1 | 3 | 0 | 4 |
| After | 4.6 | 51 | 39 | 4 | 5 | 0 | 1 |
| Joseph | | | | | | | |
| Before | 4.8 | 66 | 28 | 2 | 0 | 1 | 3 |
| After | 6.2 | 41 | 48 | 7 | 4 | 0 | 0 |
| Robert | | | | | | | |
| Before | 3.7 | 69 | 24 | 0 | 3 | 0 | 4 |
| After | 10.3 | 44 | 48 | 4 | 4 | 0 | 0 |
| Tom | | | | | | | |
| Before | 4.5 | 74 | 22 | 0 | 1 | 0 | 3 |
| After | 6.2 | 57 | 34 | 8 | 1 | 0 | 0 |
| Tim | | | | | | | |
| Before | 2.6 | 74 | 19 | 0 | 1 | 0 | 6 |
| After | 7.1 | 51 | 42 | 1 | 5 | 0 | 1 |
| Kevin | | | | | | | |
| Before | 3.1 | 65 | 21 | 0 | 8 | 0 | 6 |
| After | 6.4 | 59 | 37 | 1 | 3 | 0 | 0 |
| Roy | | | | | | | |
| Before | 3.64 | 78 | 15 | 0 | 2 | 0 | 5 |
| After | 6.9 | 54 | 35 | 8 | 3 | 0 | 0 |
| Don | | | | | | | |
| Before | 4.31 | 60 | 30 | 0 | 6 | 0 | 4 |
| After | 4.9 | 59 | 40 | 0 | 1 | 0 | 0 |
| Howard | | | | | | | |
| Before | 5.6 | 81 | 15 | 0 | 2 | 0 | 2 |
| After | 7.2 | 58 | 38 | 1 | 3 | 0 | 0 |
| Ole | | | | | | | |
| Before | 1.75 | 71 | 20 | 1 | 2 | 0 | 6 |
| After | 3.8 | 60 | 36 | 1 | 3 | 0 | 0 |

What is claimed is:

1. A method of treating a human patient to effect the remission of symptoms associated with AIDS, which comprises parenterally administering, in multiple injections, to the patient in need of such treatment typhoid vaccine in a therapeutically effective amount which is sufficient to provide immunostimulating activity, wherein
   at least one subsequent administration occurs between three (3) and twenty eight (28) days after the first administration, and
   wherein more than one subsequent administration of typhoid vaccine is given, with at least one of the subsequent administrations occurring between three (3) and twenty eight (28) days after a previous administration, and
   wherein a series of said subsequent administrations is provided over a period of at least about four (4) weeks or longer.

2. The method of claim 1, wherein a chemotherapeutic agent is administered during or after said series of subsequent administrations of typhoid vaccine.

3. A method of treating a human patient to effect the remission of symptoms associated with AIDS, which comprises parenterally administering, in multiple injections, to said patient in need of such treatment typhoid vaccine in an amount to produce substantial clumping when evaluated in an agglutination test, and wherein
   at least one subsequent administration occurs between three (3) and twenty eight (28) days after the first administration.

4. The method of claim 3 wherein more than one subsequent administration of typhoid vaccine is given, with at least one of the subsequent administrations occurring between three (3) and twenty eight (28) days after a previous administration.

5. The method of claim 4, wherein a series of subsequent administrations is provided over a period of about 4 weeks or longer.

6. The method of claim 5, wherein a chemotherapeutic agent is administered during or after said series subsequent administrations of typhoid vaccine.

7. A method of treating a human patient to effect the remission of symptoms associated with an immunosuppressing disease, which comprises parenterally administering, in multiple injections, to the patient in need of such treatment typhoid vaccine in a therapeutically effective amount which is sufficient to provide immunostimulating activity.

8. The method of claim 7 where at least one subsequent administration occurs between three (3) and twenty eight (28) days after the first administration.

9. The method of claim 7 wherein more than one subsequent administration of typhoid vaccine is given, with at least one of the subsequent administrations occurring between three (3) and twenty eight (28) days after a previous administration.

10. The method of claim 9, wherein a series of subsequent administrations is provided over a period of about 4 weeks or longer.

11. The method of claim 10, wherein a chemotherapeutic agent is administered during or after said series of subsequent administrations of typhoid vaccine.

12. A method of treating a human patient to effect the immunization against AIDS, which comprises parenterally administering, in multiple injections, to the patient typhoid vaccine in a therapeutically effective amount sufficient to provide immunostimulating activity.

13. The method of claim 12 wherein a subsequent administration is given within about three (3) months after the first administration.

* * * * *

UNITED STATES PATENT AND TRADEMARK OFFICE
CERTIFICATE OF CORRECTION

PATENT NO. : 5,116,814  Page 1 of 1
DATED : May 26, 1992
INVENTOR(S) : Salvatore J. Catapano It is certified that error appears in the above-identified patent and that said Letters Patent is hereby corrected as shown below:

<u>Title page,</u>
Item [*] Notice, should read
-- [*] Notice: The portion of the term of this patent subsequent to Dec, 5, 2005 has been disclaimed. --

Signed and Sealed this

Third Day of August, 2004

JON W. DUDAS
*Acting Director of the United States Patent and Trademark Office*